United States Patent [19]

Gennari

[11] Patent Number: 4,973,678

[45] Date of Patent: Nov. 27, 1990

[54] SALTS OF 5'-METHYLTHIO-5'-DEOXYADENOSINE WITH LONG-ALKYL CHAIN SULPHONIC ACIDS

[75] Inventor: Federico Gennari, Truccazzano, Italy

[73] Assignee: NB Jackets de Puerto Rico, Caguas, P.R.

[21] Appl. No.: 798,847

[22] Filed: Nov. 18, 1985

[30] Foreign Application Priority Data

Dec. 6, 1984 [IT] Italy ................................ 23931 A/84

[51] Int. Cl.$^5$ .......................................... C07H 19/167
[52] U.S. Cl. ........................................ 536/26; 536/24
[58] Field of Search ............................ 536/26; 514/46

[56] References Cited

U.S. PATENT DOCUMENTS 4,465,672  8/1984  Gennari ................................. 514/46

FOREIGN PATENT DOCUMENTS 2074446  11/1981  United Kingdom .

OTHER PUBLICATIONS

Kochetkov et al., Organic Chemistry of Nucleic Acids, Part A, Plenum Press, 1971, pp. 147–150, especially 149–150.

*Primary Examiner*—John W. Rollins
*Assistant Examiner*—L. Eric Crane
*Attorney, Agent, or Firm*—Michael Ebert

[57] ABSTRACT

New salts of 5'-methylthio-5'-deoxyadenosine (MTA) with long-alkyl chain sulphonic acids, which possess central and peripheral vaso-dilatory, platelet antiaggregation, antiinflammatory, analgesic and antipyretic activity.

Said salts are produced by dissolving the sodium salt of the chosen sulphonic acid in distilled water, dissolving the MTA in distilled water to which $H_2SO_4$ has been added, reacting together the two solutions to precipitate the MTA sulphonate, and recovering this latter salt with a high degree of purity.

7 Claims, No Drawings

SALTS OF 5'-METHYLTHIO-5'-DEOXYADENOSINE WITH LONG-ALKYL CHAIN SULPHONIC ACIDS

This invention relates to new salts of 5'-methylthio-5'-deoxyadenosine (MTA) with long-alkyl chain sulphonic acids, having the following general formula

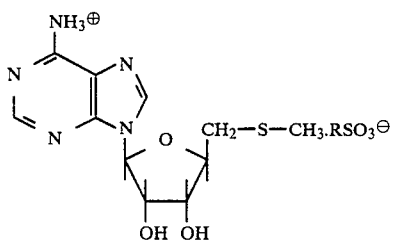

in which R is a linear or branched alkyl radical containing 6–18 carbon atoms.

The invention also relates to the process for producing said salts and to the pharmaceutical forms containing said salts as active principle.

Their possible therapeutic applications make these salts of considerable interest.

They possess central and peripheral vasodilatory activity, platelet antiaggregation activity, antiinflammatory, analgesic and antipyretic activity, and can find clinical application in the treatment of cerebral and peripheral vasculopathies of the presenile and senile age, in which the atherosclerotic degenerative process in the vasal wall alters the hematic flow, with negative consequences for the microcirculation.

In this context, the antiaggregation activity also plays an important role in that it prevents extension of intimal degenerative lesions.

The MTA salts according to the present invention can be presented either in injectable forms or in oral formulations as tablets, pills, capsules, sustained-release capsules, sustained-release tablets, gastroresistant tablets, sachets, syrups, extemporaneous syrups, sustained-release syrups and other forms normally used in pharmaceutics.

Other pharmaceutical forms can also be provided such as suppositories, creams, ointments and unguents.

The process for producing the MTA salts according to the present invention is characterised by dissolving the sodium salt of the chosen sulphonic acid in distilled water, dissolving the MTA in distilled water to which concentrated $H_2SO_4$ has been added, reacting together the two solutions to precipitate the MTA sulphonate, and recovering said salt with a high degree of purity.

These and other characteristics of the process according to the present invention, and of the products obtained and the relative pharmaceutical formulations, will be more apparent from the detailed description given hereinafter together with the examples, which are described for non-limiting illustrative purposes only.

The MTA salts according to the present invention can be easily prepared by operating in accordance with the following stages:
  preparation of MTA;
  preparation of the sodium salt of the chosen sulphonic acid;
  precipitation of the MTA salt by bringing the solutions of the products of the two preceding stages into contact;
  filtering off and drying the MTA salt.

The MTA is preferably prepared by the process of the present applicant (U.S. Pat. No. 4,454,122) by which bread yeast cells enriched in S-adenosylmethionine is lysed by treatment with ethyl or methyl acetate, the solution is concentrated under vacuum at 35°–40° C., the S-adenosylmethionine is hydrolysed by boiling under reflux, the pH is adjusted to 7 and finally the solution is cooled to 0°–5° C. and the precipitated MTA recovered.

The sulphonic acid sodium salts are preferably prepared by the process described in Italian patent application No. 20940 A/84 of the present applicant, by which the relative bromoalkanes to which water and alcohol have been added are treated with sodium sulphite while boiling under reflux. On termination of the reaction, which proceeds in accordance with the chemical equation $RBr + Na_2SO_3 \rightarrow RSO_3Na + NaBr$, the product mixture is diluted with distilled water, heated until complete dissolution, and crystallised at 15° C. The product is filtered off, washed with water and then with acetone, suspended in acetone and heated in order to extract the fatty alcohol by-product. The product is cooled, filtered, washed with acetone and dried under vacuum.

The MTA salt is prepared by the following process:
  the sodium salt of the chosen sulphonic acid is dissolved in the minimum quantity of distilled water, possibly heating to a temperature of 35°–60° C. to favour dissolution, the precise water quantities used per mole of sulphonate being as follows: 3 liters for hexanesulphonate, 10 liters for octanesulphonate, 15 liters for decanesulphonate, 20 liters for dodecanesulphonate, 30 liters for tetradecanesulphonate, 40 liters for hexadecane-sulphate and 50 liters for octadecanesulphonate;
  the MTA is dissolved in distilled water containing sulphuric acid, possibly heating to a temperature of 40°–60° C., the distilled water being in the region of 3 liters per mole of MTA and the sulphuric acid being in the region of 0.5 moles per mole of MTA;
  the MTA solution cooled to 15°–25° C. is added under agitation to the sulphonic acid sodium salt solution at a temperature of between 35° and 60° C., the two reagents being in equimolar quantities, the mixture being kept under agitation and cooled to a temperature of 15°–25° C. for a time of between 0.5 and 20 hours, and preferably for a time of between 3 and 4 hours, in order to transform the obtained MTA salt from amorphous to microcrystalline;
  the MTA salt is separated preferably by pressure filtration or centrifuging, it is washed carefully with distilled water and dried under vacuum, using a residual pressure of less than 1 mmHg, at a temperature of 40° C.

The yield varies from 80% to 95% according to the type of salt; the purity of the obtained salt exceeds 99%.

EXAMPLE 1

Preparation of MTA hexanesulphonate 18.85 kg (100 moles) of sodium hexanesulphonate are dissolved in 300 liters of distilled water at 40° C.

29.7 kg (100 moles) of MTA are dissolved in a further separate 300 liters of distilled water containing 4.9 kg (50 moles) of concentrated sulphuric acid. The mixture is heated to 50° C. to favour dissolution, and then cooled to 20° C.

This latter solution is added under agitation to the sodium hexanesulphonate solution, and the mixture cooled to 20° C.

It is left under agitation for 3 hours. A crystalline precipitate is obtained, which is filtered off in a filter press and washed with 50 liters of distilled water. The mother liquors are collected and concentrated to a volume of 100 liters.

This concentrate is cooled to 20° C. and left under agitation for 3 hours.

A white microcrystalline precipitate is obtained, which is filtered off in a pressure filter and washed with 10 liters of distilled water.

The two precipitates obtained in this manner are placed in a dryer under vacuum at 40° C. and 0.5 mmHg of residual pressure until the residual product moisture content is 2%.

37 kg of white powder are obtained, which on analysis shows the following composition:
MTA: 63%
Hexanesulphonic acid: 35%
$H_2O$: 2%
Yield = 79.9%.

The product is in the form of a white powder which is relatively poorly soluble in water but soluble in methanol and ethanol.

On HPLC analysis (column PARTISIL 10 SCX, eluent 0.2M ammonium formate, pH=4, throughput 1 ml/min) the product shows a single peak with a retention time of 350 seconds, exactly corresponding to that of the basic MTA.

| Elementary analysis: | $C_{11}H_{15}N_5O_3S.C_6H_{14}O_3S$ | | |
|---|---|---|---|
| | N | C | H |
| Calculated % | 15.1 | 44.05 | 6.3 |
| Found % | 15.1 | 44.1 | 6.4 |

The product ultraviolet spectrum (3 mg in 100 ml 1N $H_2SO_4$) shows an absorption maximum at 257 nm with $E_{1\%} = 321$.

EXAMPLE 2

Preparation of MTA octanesulphonate 21.65 kg of sodium octanesulphonate (100 moles) are dissolved in 1000 liters of distilled water at 40° C.

The procedure of Example 1 is followed until the product is completely dry. 40 kg of white powder are obtained which on analysis shows the following composition:
MTA: 59.3%
Octanesulphonic acid: 38.7%
$H_2O$: 2%
Yield = 81.4%

The product is in the form of a white powder which is relatively poorly soluble in water but soluble in methanol and ethanol.

On HPLC analysis (column PARTISIL 10 SCX, eluent 0.2M ammonium sulphate, pH=4, throughput 1 ml/min) the product shows a single peak with a retention time of 350 seconds, exactly corresponding to the basic MTA.

| Elementary analysis: | $C_{11}H_{15}N_5O_3S.C_8H_{18}O_3S$ | | |
|---|---|---|---|
| | N | C | H |
| Calculated % | 14.25 | 46.4 | 6.8 |
| Found % | 14.3 | 46.5 | 6.8 |

The product ultraviolet spectrum (3 mg in 100 ml 1N $H_2SO_4$) shows an absorption maximum at 257 mn with $E_{1\%} = 302$.

EXAMPLE 3

Preparation of MTA decanesulphonate 24.45 kg of sodium decanesulphonate (100 moles) are dissolved in 1500 liters of distilled water at 40° C.

The procedure of Example 1 is followed until the product is completely dry. 44.5 kg of white powder are obtained, which on analysis shows the following composition:
MTA: 56.1%
Decanesulphonic acid: 41.9%
$H_2O$: 2%
Yield = 85.6%

The product is in the form of a white powder which is poorly soluble in water but soluble in methanol and ethanol.

On HPLC analysis (column PARTISIL 10 SCX, eluent 0.2M ammonium formate, pH=4, throughput 1 ml/min) the product shows a single peak with a retention time of 350 seconds, exactly corresponding to that of the basic MTA.

| Elementary analysis: | $C_{11}H_{15}N_5O_3S.C_{10}H_{22}O_2S$ | | |
|---|---|---|---|
| | N | C | H |
| Calculated % | 13.5 | 48.5 | 7.2 |
| Found % | 13.5 | 48.5 | 7.1 |

The product ultraviolet spectrum (3 mg in 100 ml 1N $H_2SO_4$) shows a maximum absorption at 257 mm with $E_{1\%} = 286$.

EXAMPLE 4

Preparation of MTA dodecanesulphonate 27.25 kg of sodium dodecanesulphonate (100 moles) are dissolved in 2000 liters of distilled water at 40° C.

29.7 kg (100 moles) of MTA are dissolved separately in 300 liters of distilled water containing 4.9 kg (50 moles) of concentrated sulphuric acid.

The mixture is heated to 50° C. to favour dissolution, and is then cooled to 20° C.

This latter solution is poured under agitation into the sodium dodecanesulphonate solution, and the mixture cooled to 20° C.

It is left under agitation for 3 hours.

A microcrystalline white precipitate is obtained, which is filtered off in a pressure filter and washed with 100 liters of distilled water.

The precipitate thus obtained is placed in a vacuum dryer at 40° C. and 0.5 mmHg of residual pressure until the residual product moisture content is 2%.

49.2 kg of white powder are obtained, which on analysis shows the following composition:
MTA: 53.2%
Dodecanesulphonic acid: 44.8%
$H_2O$: 2%
Yield = 89.9%

The product is in the form of a white powder which is insoluble in water but soluble in methanol, ethanol and 2:1 methanol-chloroform mixtures. On HPLC analysis (column PARTISIL 10 SCX, eluent 0.2M ammonium formate, pH=4, throughput 1 ml/min) the product shows a single peak with a retention time of 350 seconds, exactly corresponding to that of the basic MTA.

| Elementary analysis: | $C_{11}H_{15}N_5O_3S \cdot C_{12}H_{26}O_3S$ | | |
|---|---|---|---|
|  | N | C | H |
| Calculated % | 12.8 | 50.4 | 7.6 |
| Found % | 12.8 | 50.3 | 7.7 |

The product ultraviolet spectrum (3 mg in 100 ml 1N $H_2SO_4$) shows an absorption maximum at 257 mn with $E_{1\%} = 271$.

EXAMPLE 5

Preparation of MTA tetradecanesulphonate 30.05 kg of sodium tetradecanesulphonate (100 moles) are dissolved in 3000 liters of distilled water at 50° C.

The procedure of Example 4 is followed until the product is completely dry. 52.9 kg of white powder are obtained, which on analysis shows the following composition:

MTA: 50.6%
Tetradecanesulphonic acid: 47.4%
$H_2O$: 2%
Yield = 91.9%

The product is in the form of a white powder which is insoluble in water but soluble in methanol, ethanol and 2:1 methanol-chloroform mixtures.

On HPLC analysis (column PARTISIL 10 SCX, eluent 0.2M ammonium formate, pH=4, throughput 1 ml/min) the product shows a single peak with a retention time of 350 seconds, exactly corresponding to that of the basic MTA.

| Elementary analysis: | $C_{11}H_{15}N_5O_3S \cdot C_{14}H_{30}O_3S$ | | |
|---|---|---|---|
|  | N | C | H |
| Calculated % | 12.2 | 52.1 | 7.9 |
| Found % | 12.1 | 52.1 | 7.9 |

The product ultraviolet spectrum (3 mg in 100 ml 1N $H_2SO_4$) shows an absorption maximum at 257 mn with $E_{1\%} = 258$.

EXAMPLE 6

Preparation of MTA hexadecanesulphonate 32.85 kg of sodium hexadecanesulphonate (100 moles) are dissolved in 4000 liters of distilled water at 60° C.

The procedure of Example 4 is followed until the product is completely dry.

56.7 kg of white powder are obtained, which on analysis shows the following composition:

MTA: 48.2%
Hexadecanesulphonic acid: 49.8%
$H_2O$: 2%
Yield = 94%

The product is in the form of a white powder which is insoluble in water but soluble in methanol, ethanol and 2:1 methanol-chloroform mixtures.

On HPLC analysis (column PARTISIL 10 SCX, eluent 0.2M ammonium formate, pH=4, throughput 1 ml/min) the product shows a single peak with a retention time of 350 seconds, exactly corresponding to that of the basic MTA.

| Elementary analysis: | $C_{11}H_{15}N_5O_3S \cdot C_{16}H_{34}O_3S$ | | |
|---|---|---|---|
|  | N | C | H |
| Calculated % | 11.6 | 53.7 | 8.2 |
| Found % | 11.6 | 53.6 | 8.2 |

The product ultraviolet spectrum (3 mg in 100 ml 1N $H_2SO_4$) shows an absorption maximum at 257 mn with $E_{1\%} = 246$.

EXAMPLE 7

Preparation of MTA octadecanesulphonate 35.65 kg of sodium octadecanesulphonate (100 moles) are dissolved in 5000 liters of distilled water at 60° C.

The procedure of Example 4 is followed until the product is completely dry.

60 kg of white powder are obtained, which on analysis shows the following composition:

MTA: 46.1%
Octadecanesulphonic acid: 51.9%
$H_2O$: 2%
Yield = 95%.

The product is in the form of a white powder which is insoluble in water, slightly soluble in methanol and ethanol, and soluble in 2:1 methanol-chloroform mixtures.

On HPLC analysis (column PARTISIL 10 SCX, eluent 0.2M ammonium formate, pH=4, throughput 1 ml/min) the product shows a single peak with a retention time of 350 seconds, exactly corresponding to that of the basic MTA.

| Elementary analysis: | $C_{11}H_{15}N_5O_3S \cdot C_{18}H_{38}O_3S$ | | |
|---|---|---|---|
|  | N | C | H |
| Calculated % | 11.1 | 55.1 | 8.5 |
| Found % | 11.2 | 55.2 | 8.5 |

The product ultraviolet spectrum (3 mg in 100 ml 1N $H_2SO_4$) shows an absorption maximum at 257 nm with $E_{1\%} = 235$.

EXAMPLE 8

Preparation of gastrosoluble tablets (a) A 200 mg tablet contains:
| | |
|---|---|
| MTA octadecanesulphonate | 434 mg |
| equivalent to a basic MTA quantity of | 200 mg |
| Cross-linked carboxymethylcellulose | 50 mg |
| Magnesium stearate | 10 mg |
| Microcrystalline cellulose to make up to | 600 mg |

(b) A 200 mg tablet contains:
| | |
|---|---|
| MTA dodecanesulphonate | 376 mg |
| equivalent to a basic MTA quantity of | 200 mg |
| Corn starch | 80 mg |
| Polyvinylpyrrolidone | 20 mg |
| Magnesium stearate | 10 mg |

(c) A 200 mg tablet contains:
| | |
|---|---|
| MTA hexadecanesulphonate | 415 mg |
| equivalent to a basic MTA quantity of | 200 mg |
| Sodium chloride | 100 mg |
| Polyvinylpyrrolidone | 20 mg |

-continued

| | |
|---|---|
| Corn starch to make up to | 650 mg |

EXAMPLE 9

Preparation of injectable solutions

A lyophilised vial contains:

| | |
|---|---|
| MTA hexanesulphonate | 79.4 mg |
| equivalent to a basic MTA quantity of | 50 mg |
| Mannitol | 100 mg |
| A solvent vial contains: | |
| Citrated buffer to make up to | pH 5 |
| Bidistilled water to make up to | 5 ml |

EXAMPLE 10

Preparation of an extemporaneous solution for oral use

A bottle contains:

| | |
|---|---|
| MTA hexanesulphonate | 159 mg |
| equivalent to a basic MTA quantity of | 100 mg |
| Saccharose | 100 mg |
| Flavourings and preservatives | |
| Bidistilled water to make up to | 10 ml |

EXAMPLE 11

Preparation of chronoids

A 100 mg capsule contains:

| | |
|---|---|
| MTA octadecanesulphonate | 217 mg |
| equivalent to a basic MTA quantity of | 100 mg |
| Sugar chronoids | 200 mg |

EXAMPLE 12

Preparation of capsules

A 100 mg capsule contains:

| | |
|---|---|
| MTA hexadecanesulphonate | 207.5 mg |
| equivalent to a basic MTA quantity of | 100 mg |
| Mannitol | 50 mg |
| Lactose | 50 mg |
| Magnesium stearate | 12 mg |

EXAMPLE 13

Preparation of suppositories

A 200 mg suppository contains:

| | |
|---|---|
| MTA octadecanesulphonate | 434 mg |
| equivalent to a basic MTA quantity of | 200 mg |
| Suppository mass to make up to | 2500 mg |

I claim:

1. New salts of 5'-methylthio-5'-deoxyadenosine (MTA) with long-alkyl chain sulphonic acids, characterised by the following general formula:

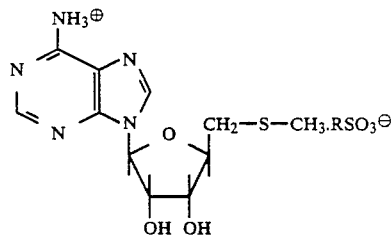

in which R is a linear or branched alkyl radical containing 6–18 carbon atoms.

2. A process for preparing salts of 5'-methylthio-5'-deoxyadenosine (MTA) with long-alkyl chain sulphonic acids, and having the following general formula:

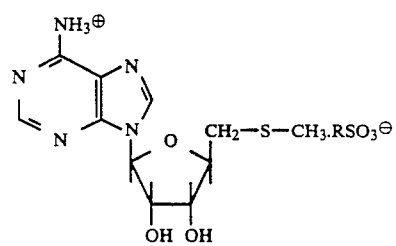

in which R is a linear or branched alkyl radical containing 6–18 carbon atoms, characterised by dissolving the sodium salt of the chosen sulphonic acid in distilled water, dissolving the MTA in distilled water to which concentrated $H_2SO_4$ has been added, reacting together the two solutions to precipitate the MTA sulphonate, and recovering this latter salt with a high degree of purity.

3. A process as claimed in claim 2, characterised in that the sulphonic acid sodium salt undergoes said dissolving at a temperature of between 35° and 60° C., using the following water quantities per mole of salt: 3 liters for hexanesulphonate, 10 liters for octanesulphonate, 30 liters for tetradecanesulphonate, 40 liters for hexadecanesulphonate and 50 liters for octadecanesulphonate.

4. A process as claimed in claim 2, characterised in that the MTA undergoes said dissolving at a temperature of between 40° and 60° C. in a mixture of distilled water and $H_2SO_4$ containing 3 liters of distilled water and 0.5 moles of $H_2SO_4$ per mole of MTA.

5. A process as claimed in claim 2, characterised in that said reaction is effected by adding the MTA solution cooled to 15°–25° C. to the sulphonic acid sodium salt solution at a temperature of between 35° and 60° C. under agitation, the two reagents being in equimolar quantities, the mixture being kept under agitation and cooled to a temperature of 15°–25° C. for a time of between 0.5 and 20 hours.

6. A process as claimed in claim 2, characterised in that the MTA sulphonate undergoes said recovery by filtration under pressure or by centrifuging followed by washing with distilled water and drying under vacuum at a temperature of 40° C.

7. Pharmaceutical compositions having central and peripheral vasodilatory, platelet antiaggregation, antiinflammatory, analgesic and antipyretic activity, comprising a therapeutically effective amount of at least one compound of general formula (I) as defined in claim 1 as their active principle and a pharmaceutically acceptable carrier.

* * * * *

UNITED STATES PATENT AND TRADEMARK OFFICE
CERTIFICATE OF CORRECTION

PATENT NO. : 4,973,678
DATED : November 27, 1990
INVENTOR(S) : Federico Gennari

It is certified that error appears in the above-indentified patent and that said Letters Patent is hereby corrected as shown below:

Title page, item [73], Assignee: should read-- Bioresearch S.p.A., Milano, Italy --.

Signed and Sealed this

Twenty-sixth Day of September, 1995

Attest:

BRUCE LEHMAN

*Attesting Officer*     *Commissioner of Patents and Trademarks*